United States Patent
McClure et al.

(10) Patent No.: US 7,239,134 B2
(45) Date of Patent: Jul. 3, 2007

(54) SCREENING METHOD AND APPARATUS

(75) Inventors: Richard J. McClure, San Diego, CA (US); Frederick J. Jeffers, Escondido, CA (US); R. Kemp Massengill, Leucadia, CA (US)

(73) Assignee: MedNovus, Inc., Leucadia, CA (US)

( * ) Notice: Subject to any disclaimer, the term of this patent is extended or adjusted under 35 U.S.C. 154(b) by 0 days.

(21) Appl. No.: 11/512,048

(22) Filed: Aug. 28, 2006

(65) Prior Publication Data

US 2007/0052411 A1 Mar. 8, 2007

Related U.S. Application Data

(63) Continuation-in-part of application No. 10/703,147, filed on Nov. 5, 2003, now Pat. No. 7,106,056, which is a continuation of application No. 10/681,033, filed on Oct. 7, 2003.

(60) Provisional application No. 60/489,250, filed on Jul. 22, 2003, provisional application No. 60/440,697, filed on Jan. 17, 2003.

(51) Int. Cl.
*G01N 27/72* (2006.01)
*G01R 33/00* (2006.01)

(52) U.S. Cl. ............... 324/232; 324/228; 324/244; 324/260

(58) Field of Classification Search ............ 324/228, 324/232, 242–243, 244, 260; 600/407, 409
See application file for complete search history.

(56) References Cited

U.S. PATENT DOCUMENTS 2,523,933 A 9/1950 Cuthbert et al.

(Continued)

FOREIGN PATENT DOCUMENTS

WO WO 03/091753 A1 11/2003

(Continued)

OTHER PUBLICATIONS

ETS-Lindgren Website; *Ferromagnetic Detection System*; May 29, 2004; 2 pages.

(Continued)

*Primary Examiner*—Bot LeDynh
(74) *Attorney, Agent, or Firm*—Gerald W. Spinks

(57) ABSTRACT

A method and an apparatus are disclosed, to screen patients or other areas for ferromagnetic objects, particularly for use intra-operatively in an operating room. The device comprises at least one magnetic field source, at least one magnetic gradiometer, and the associated electronics. The field source and the gradiometer are supported by an arm structure which can be manipulated to position the field source and the gradiometer at one or more positions near areas of interest, such as areas on a patient or other subject, and to orient the field source and the gradiometer so that the axis of the magnetic field is arranged along three different non-parallel, non-coplanar, axes to ensure detection of any ferromagnetic object regardless of its shape and orientation. The device can be manipulated to place the sensor arrays in close proximity to selected parts of a subject's body, for screening purposes. Two field sources and two gradiometers can be provided, for positioning on two sides of a portion of the subject's body, such as the head.

21 Claims, 8 Drawing Sheets

U.S. PATENT DOCUMENTS

| | | |
|---|---|---|
| 3,364,840 A | 1/1968 | Allen |
| 3,781,664 A | 12/1973 | Rorden |
| 3,869,967 A | 3/1975 | Lenz |
| 3,971,983 A | 7/1976 | Jaquet |
| 4,060,039 A | 11/1977 | Lagarrigue |
| 4,068,164 A | 1/1978 | Schwartz et al. |
| 4,135,183 A | 1/1979 | Heltemes |
| 4,193,024 A | 3/1980 | Hoult et al. |
| 4,734,643 A | 3/1988 | Bubenik et al. |
| 4,837,489 A | 6/1989 | McFee |
| 4,990,850 A | 2/1991 | Votruba |
| 5,119,025 A | 6/1992 | Smith et al. |
| 5,175,419 A | 12/1992 | Yamashita |
| 5,260,653 A | 11/1993 | Smith et al. |
| 5,321,361 A | 6/1994 | Goodman |
| 5,327,846 A | 7/1994 | Androus |
| 5,379,334 A | 1/1995 | Zimmer et al. |
| 5,397,986 A | 3/1995 | Conway et al. |
| 5,408,178 A | 4/1995 | Wikswo, Jr. et al. |
| 5,493,517 A | 2/1996 | Frazier |
| 5,494,033 A | 2/1996 | Buchanan et al. |
| 5,494,035 A | 2/1996 | Leuthold et al. |
| 5,504,428 A | 4/1996 | Johnson |
| 5,588,386 A | 12/1996 | Schilt |
| 5,610,518 A | 3/1997 | Chamberlain, IV |
| 5,689,184 A | 11/1997 | Jeffers et al. |
| 5,705,924 A | 1/1998 | Jeffers |
| 5,735,278 A | 4/1998 | Hoult et al. |
| 5,757,183 A | 5/1998 | Smith et al. |
| 5,842,986 A | 12/1998 | Avrin |
| 6,064,208 A | 5/2000 | Steckner |
| 6,087,832 A | 7/2000 | Doty |
| 6,133,829 A | 10/2000 | Johnstone et al. |
| 6,150,810 A | 11/2000 | Roybal |
| 6,208,884 B1 | 3/2001 | Kumar et al. |
| 6,362,739 B1 | 3/2002 | Burton |
| 6,384,603 B2 | 5/2002 | Hoult et al. |
| 6,418,335 B2 | 7/2002 | Avrin et al. |
| 6,496,713 B2 | 12/2002 | Avrin et al. |
| 6,541,966 B1 | 4/2003 | Keene |
| RE38,157 E | 6/2003 | Schneider |
| 6,670,809 B1 | 12/2003 | Edelstein et al. |
| 6,828,892 B1 | 12/2004 | Fukushima et al. |
| 6,956,369 B2 | 10/2005 | Czipott et al. |
| 6,965,792 B2 | 11/2005 | Avrin et al. |
| 7,013,245 B2 | 3/2006 | Kotter et al. |
| 7,106,056 B2 | 9/2006 | Czipott et al. |
| 7,113,092 B2 | 9/2006 | Keene |
| 2002/0115925 A1 | 8/2002 | Avrin et al. |
| 2002/0151779 A1 | 10/2002 | Avrin et al. |
| 2003/0083588 A1 | 5/2003 | McClure et al. |
| 2003/0171669 A1 | 9/2003 | Kopp |
| 2003/0216632 A1 | 11/2003 | McClure et al. |
| 2004/0135687 A1 | 7/2004 | Keene |
| 2004/0147833 A1 | 7/2004 | Czipott et al. |
| 2004/0189293 A1 | 9/2004 | Czipott et al. |
| 2005/0242817 A1 | 11/2005 | Hoult |
| 2006/0022670 A1 | 2/2006 | Kumar et al. |
| 2006/0084857 A1 | 4/2006 | Massengill et al. |
| 2006/0139025 A1 | 6/2006 | Jeffers |
| 2006/0145691 A1 | 7/2006 | Massengill et al. |
| 2006/0158331 A1 | 7/2006 | Massengill et al. |

FOREIGN PATENT DOCUMENTS

| | | |
|---|---|---|
| WO | WO 2004/044620 A1 | 5/2004 |

OTHER PUBLICATIONS

ETS-Lindgren; *Ferroguard Unveiled at RSNA 2003*; The Quiet Zone; Jan. 2004; p. 11.

Finn, Edward J., et al., *Ferromagnetic Materials in Patients: Detection before MR Imaging*; Radiology; Jul. 1985; vol. 185; pp. 139-141.

Institute for Biodiagnostics; *MRI Safety: Detection of Ferromagnetic Objects*; Date unknown; 8 pages; National Research Council Canada.

Kopp Development; Ferralert Brochure; Date Unknown; 2 pages; Kopp Development; Jensen Beach, FL.

Kotter, David K., et al..; Abstract: *Detection and Classification of Concealed Weapons Using a Magnetometer-based Portal*; NASA ADS Instrumentation Abstract Service; Aug. 2002; 1 page; The International Society for Optical Engineering.

Mednovus/Quantum Magnetics; Safescan Portal 9000 Series Brochure; 1 page.

*Melodi Metal Locator Gets Straight to the Point*; Medica 2002; Nov. 2002; 4 pages; Düsseldorf, Germany.

*Metal Detector Finds Lost Coins in Kids*; CNN.com/TECHNOLOGY; Jan. 29, 2003;2 pages; Cable News Network.

Quantum Magnetics; i-portal 100 Advanced Weapons Detection Portal Brochures; Date unknown; 8 pages.

CMP United Business Media Website; Metal detector guards the door to screen ferromagnetic objects; Diagnostic Imaging Scan; Jan. 28, 2004; 2 pages.

though the integrated magnetic moment of the gurney or cart can be significant, the detectability of these components is limited because of the difficulty of concentrating the magnetic field produced by the traditional detection portal precisely on the offending components. In addition to concentration of the field, it would be helpful to be able to provide a second pass of the portal over the object, to determine whether a signal was in fact present and reproducible.

SCREENING METHOD AND APPARATUS

CROSS REFERENCE TO RELATED APPLICATIONS

This is a continuation-in-part application of U.S. application Ser. No. 10/703,147, filed Nov. 05, 2003 now U.S. Pat. No. 7,106,056, for "Security Screening Method and Apparatus", which is a continuation application of copending U.S. application Ser. No. 10/681,033, filed Oct. 07, 2003, for "Magnetic Resonance Imaging Screening Method and Apparatus". This is also a continuation-in-part application of co-pending U.S. Application Ser. No. 10/681,033, filed Oct. 7, 2003, for "Magnetic Resonance Imaging Screening Method and Apparatus". The parent applications also rely upon U.S. Provisional Pat. App. No. 60/440,697, filed Jan. 17, 2003, for "Method and Apparatus to Use Magnetic Entryway Detectors for Pre-MRI Screening", and U.S. Provisional Pat. App. No. 60/489,250, filed Jul. 22, 2003, for "Ferromagnetic Wand Method and Apparatus for Magnetic Resonance Imaging Screening".

STATEMENT REGARDING FEDERALLY SPONSORED RESEARCH OR DEVELOPMENT

Not Applicable

BACKGROUND OF THE INVENTION

1. Field of the Invention

The present invention is in the field of methods and apparatus used to prevent the presence of paramagnetic or ferromagnetic objects near a magnetic resonance imaging (MRI) system.

2. Background Art

Paramagnetic and ferromagnetic objects are highly unsafe near MRI systems, because the strong magnetic gradients caused by MRI magnets exert a strong force on such objects, potentially turning them into dangerous missiles. Several accidents, some fatal, are known to have occurred as the result of someone inadvertently carrying such an object into the MRI room. Current MRI safety practices rely on signage and training to prevent people from taking such objects into the MRI chamber. There is a need for a technical means to prevent the accidental transportation of such objects into the MRI chamber, or to warn of such an occurrence.

Use of conventional metal detectors, whether portals or wands, would not be efficient for this purpose, because they do not distinguish between magnetic and non-magnetic objects, and only magnetic objects are dangerous. Conventional systems generate an audio-band oscillating or pulsed magnetic field with which they illuminate the subject. The time-varying field induces electrical eddy currents in metallic objects. It is these eddy currents which are detected by the system, to reveal the presence of the metallic objects. There is no discrimination between ferromagnetic objects, which are dangerous near an MRI system, and non-magnetic objects, which are not. As a result, conventional systems would generate far too many false alarms to be usable in this application. The invention described herein solves the problem by detecting only paramagnetic and ferromagnetic objects, which are exactly those that must be excluded from the MRI room.

The present invention specifically addresses a need for intra-operative application of MRI. The current surgical technique for most major cancer surgical procedures is for the surgeon to remove the tumor as delineated by the preoperative MRI. Upon conclusion of what is believed to be adequate tumor excision, the skin incision is sutured, and the patient is sent to recovery. A postoperative MRI is then performed in the imaging center, and, it is hoped, no residual tumor is found.

Unfortunately, residual tumor is commonly present. Neurosurgery is a field in which the use of MRI is ubiquitous. With conventional neurosurgery, in an effort to make certain that "all the cancer" is removed, neurosurgeons often excise significant sections of normal brain tissue, recognizing that it is difficult to determine visually the exact borders of the cancer, even with the use of an operating microscope.

When the cancer is incompletely excised during the initial neurosurgical procedure, however, as documented by postoperative MRI after the patient is sent to recovery, the patient is returned to the operating room for further surgery. This is often on a different day than the first surgical procedure, causing tremendous anxiety to the patient and to the patient's family.

The patient must be re-anaesthetized, the craniotomy flap reopened, and more brain tissue excised, in the hope that the tumor has been completely extirpated. A postoperative MRI is obtained to confirm or deny this.

The use of intra-operative MRI can change the hit-or-miss scenario described above, and a number of centers have established intra-operative MRI facilities. The advantage of intra-operative MRI is similar in concept to that of Moh's procedure for skin cancers, in which sequential intra-operative biopsies of tumor margins are examined by a pathologist and determined to be cancer-free before the surgery is concluded and the incision is sutured. The difference is that with intra-operative MRI, confirmation of the tumor margin is made not by pathological microscopic examination of excised tissue, but by magnetic resonance imaging.

Two competing methodologies are becoming available to accommodate intra-operative MRI. In the first methodology, the MRI magnet is brought into the operating room on a mechanized retractable transport tube. The operating room table remains stationary, and intra-operative MRI is performed ("mountain-to-patient strategy"). After intra-operative MR imaging, the transport tube is retracted into the adjacent room, and the surgery continues, based upon information gleaned from the intra-operative MRI. This procedure can be repeated until the surgeon and his or her team are completely satisfied that the tumor has been completely eliminated.

The second methodology involves bringing the patient to the MRI magnet, which is in a separate dedicated ante-room. In this instance, the MRI suite can be used for other intra-operative MRI procedures, as the ante-room can be fed, as it were, by one or more operating room theatres. This second ("patient-to-mountain") strategy requires that the OR table and the anesthesia cart to which the patient is obligatorily attached be transported into the magnet room.

In either strategy, it would be helpful to be able to thoroughly scan the patient, and the operating room table and anesthesia cart for ferromagnetic threat objects. To minimize the missile threat in the intra-operative scenario described herein, the use of very sensitive ferromagnetic-only detection portals may well prove beneficial.

A major problem at this time, however, is that even so-called "MRI Safe" pieces of equipment, such as designated gurneys, anesthesia carts, and the like, often contain small ferromagnetic components, such as wheel bearings, or gauge displays on monitoring equipment. Because of the very large mass of the gurney or cart relative to the very small amount of ferromagnetic materials present, however, the gurney or cart is not propelled toward the MRI magnet. Nevertheless, the ferromagnetic material will trigger a false-positive alarm when the gurney or cart passes through a sensitive ferromagnetic detection portal. This alarm response is baffling to the surgeon, as he or she cannot know whether the alarm emanates from the gurney or cart, or from a true ferromagnetic threat with the potential for causing harm.

A worrisome threat is a ferromagnetic hemostat clamp deep within the abdomen of a patient undergoing cancer surgery. If the surgeon is unaware of the presence of this clamp, and intra-operative MRI proceeds, the magnetic field of the MRI instrument could cause the clamp to tear through the patient's tissues, causing hemorrhage, nerve damage, and other catastrophically untoward consequences.

Many surgical instruments are non-magnetic and non-magnetizable, but not all. Of course, with intra-operative surgery employing MRI, a great effort should be made to have all instruments in the surgical environment be non-magnetic and non-magnetizable, but this is not always practical.

What is required, then, is a ferromagnetic detection system which detects these ferromagnetic instruments before the intra-operative MRI procedure. The present invention provides an apparatus and method for achieving this requirement. In addition to intra-operative MRI, the present invention can be employed for the detection of foreign objects within a patient prior to conventional MRI. It can also detect ferromagnetic threat objects on the person of a subject, such as bobby pins or nail clippers.

BRIEF SUMMARY OF THE INVENTION

The present invention provides an apparatus and a method for scanning a patient, or other subject, as well as any associated object such as an operating table, for the presence of an object which is either permanently magnetic or susceptible to being magnetized by an external field. A magnetic sensor pair and magnetic field source in this scanning apparatus can be mounted on the free end of an arm which can be manipulated into various configurations to position the sensor pair and the field source at one or more selected positions near the subject, to orient the sensor pair and field source so that the axis of the magnetic field is arranged along one or more selected axes at each selected position, and to move the sensor pair and field source along each selected axis. This positions the field source and the sensor pair in proximity to every selected portion of a patient or other subject or object. Two sensor pairs and two associated field sources can be provided, spaced apart on a frame on the support arm, to allow positioning of a first sensor pair and a first field source on one side of a portion of the subject, while simultaneously positioning a second sensor pair and a second field source on another side of that portion of the subject.

The sensors in the apparatus of the present invention can detect the magnetic field of a ferromagnetic object, whether the object is a permanent magnet or merely susceptible to magnetization by the magnetic field source.

Positioning and movement of the detection head, consisting of a magnetization source, the sensor elements, and possibly part, or all, of the associated electronics, can be manually controlled or motor driven. Although motorized control can be used to direct the screening movements of the detection head configuration, hand direction and manipulation of the detection head configuration is usually preferred, because the use of motors to direct movement can introduce noise, thereby degrading the signal being sensed.

If ferromagnetic detection is required at a significant depth, the detection head configuration is usually larger, especially if a permanent magnet source (flexible or non-flexible) is used. This is because ferromagnetic detection at a greater distance, such as of the intra-abdominal region, generally requires a magnet of greater dimensions than that required for ferromagnetic detection at a closer distance, such as of the skull/brain area.

It is a general rule that the magnetic field magnitude scales with the volume of the magnet.

The present invention can be configured as a DC sensing system, or as an AC sensing system. Both sense magnetic fields, but in different ways. A detection head configuration, consisting of a magnetization source, the sensor elements, and possibly part, or all, of the associated electronics, is positioned as closely as possible to the detection region of interest. The detection head configuration can have a non-ferromagnetic casing. Positioning the detection head configuration as close to the ferromagnetic threat object as possible is very important, as this greatly increases detectability.

Ferromagnetic detection proceeds sequentially one axis at a time in the x, y, and z axes. The axes need not be perfectly orthogonal to each other; the operator can simply approximate movement along orthogonal axes, as long as the axes are not parallel to each other. If desired, the screening movements can be performed first from one starting position, such as from above, and then from a different starting position, such as from the side of the patient. As the direction of magnetization from the magnetizing source is different from the first starting position to the second position, greater reliability and a diminished chance of a false negative can be obtained in this fashion.

Adding body movement, when feasible, such as having the patient actively tilt and/or rotate his or her head, or, alternatively, having the technician perform these movements on the patient, increases the likelihood of ferromagnetic detection and diminishes the possibility of a false negative.

A frame support structure allowing movement provides stabilization and promotes orderly screening movements and ease of use. For applications in intra-operative MRI, the present invention should be tethered, such as to the wall, the ceiling, or to a large immoveable object, so that it does not become a projectile missile.

A "floating arm" configuration, comprised of frame support members and one or more appropriately-designed joint articulations, allows unencumbered movements of the detection head configuration, with the goal of performing multi-axis ferromagnetic detection, screening in sequence first along one axis, and then the next, until all 3 axes are screened.

The joint articulations can be of a flexible goose-neck material, or can be ball-joints, or other types of joint articulation allowing movement, or a combination of these components. The frame support structure members and the joint articulations are preferably non-ferromagnetic, as ferromagnetic moving parts in the close vicinity of the detection head configuration can trigger false alarms.

The preferred movements of the detection head configuration are smooth, orderly, and systematic, as these are more effective for finding occult ferromagnetic threats than jerky or haphazard movements.

The sensors are preferably configured in gradiometer format to minimize, or eliminate, unwanted signals from distant moving ferromagnetic sources, such as elevators, chairs, or cars moving in a parking garage or a near-by street. An alarm, preferably with both audio and visual components, is activated whenever a ferromagnetic threat object is detected. If desired, an interlock can be provided, preventing access into the MRI magnet room or energization of the MRI magnet.

The instrument can be configured in a completely analog version. Digitizing the signal, however, allows greater flexibility and the use of signal processing algorithms, including neural nets and other expert systems, to improve the sensitivity of the system and its ferromagnetic detection characteristics.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
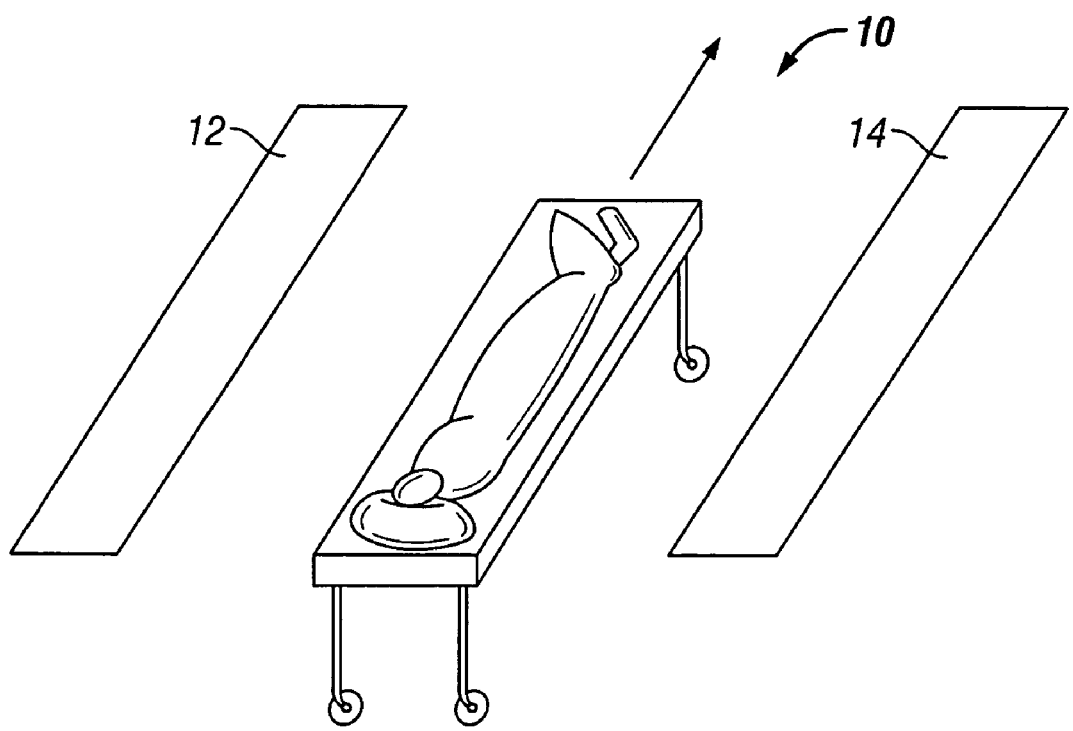
FIG. 1 is a schematic showing the horizontal arrangement of sensor arrays in a first portal type arrangement disclosed in the parent patent applications.

The present invention, which applies to both permanently magnetic objects and non-permanent magnetically susceptible objects, can use magnetometers with good sensitivity at frequencies all the way, or nearly, to DC, i.e., zero frequency. This allows several modes of use:

(1) A completely passive system detects ferromagnetic objects using their permanent magnetization, or the magnetization induced by the Earth's magnetic field.

(2) A system can apply a DC magnetic field, allowing control and usually enhancement of the magnetization of objects, thus enhancing their detectability.

(3) An AC magnetic susceptometer applies an oscillating AC magnetic field, but at very low frequencies compared to conventional detectors, allowing enhancement of their magnetization. The purpose of AC illumination is to move the signal from DC to a region of lower noise at finite frequency. The AC frequency is chosen to avoid inducing the electrical eddy currents detected by other systems, to suppress the response from non-ferromagnetic metal objects, and thus maintaining the discrimination capability.

An array of sensors can be arranged in such a way that the entire sensor array can be placed in proximity to all portions of the body of a subject, such as a patient or an attendant. In particular, the sensor arrays are arranged so as to be susceptible to placement in proximity to all portions of the body of a patient lying recumbent, as on a stretcher or gurney. This object is accomplished by either a portal structure or a hand held wand. The portal structure is designed to have one or more horizontally arranged sensor arrays, suitable for alignment of the entire sensor array with a recumbent patient. This differs from a portal arrangement in which the sensor arrays are arranged vertically, placing only a few of the sensors in proximity to a recumbent patient. The wand is susceptible to movement over the body of the subject in order to place the entire sensor array in proximity to all portions of the subject's body.

A passive magnetic portal can be somewhat similar to the SecureScan 2000™ weapons detection portal which is manufactured by Quantum Magnetics, Inc., and marketed by Milestone Technology, Inc., or the i-Portal™ weapons detection portal which is marketed by Quantum Magnetics, Inc. In important respects, however, the portal would be modified to be suitable for use, namely, to make it suitable for use with a recumbent subject lying on a gurney or stretcher, rather than walking upright. In the known configuration, patients on gurneys would be too distant from too many of the sensors for adequate detection.

Such a portal includes two panels of sensors on the sides of the entryway. An array of magnetometers inside each panel enables detection, characterization, and localization of ferromagnetic objects from the soles of the feet to the top of the head. The magnetometer array can take a variety of configurations, and it can use a variety of sensor technologies. For example, a set of 16 single-axis magnetic gradiometers can be arranged with 8 in each panel. Other configurations can include arrays of multi-axis gradiometers, or combinations of single-axis and multi-axis gradiometers. One or more magnetic tensor gradiometers may also be used. A magnetoresistive magnetometer, or any other sensor capable of sensing magnetic field changes at or near zero frequency, can be used.

As shown in FIG. 1, in order to scan a patient on a gurney, the portal sensor configuration 10 must be arranged to bring all of the sensors closer to the patient and to effectively scan a patient in the recumbent position. Rather than being arranged vertically as in the aforementioned known portals, the two sensor panels 12, 14 can be arranged horizontally, parallel to the path of the gurney and on either side, as shown in FIG. 1. This places the sensors in a similar relation to the patient as they would have, in the vertical arrangement, to an ambulatory patient. Also, a single "snapshot" of data covers the entire gurney and patient, as in the ambulatory case. The sensor panels 12, 14 can be permanently arranged horizontally, or they can pivot to this configuration.

Figure 2:
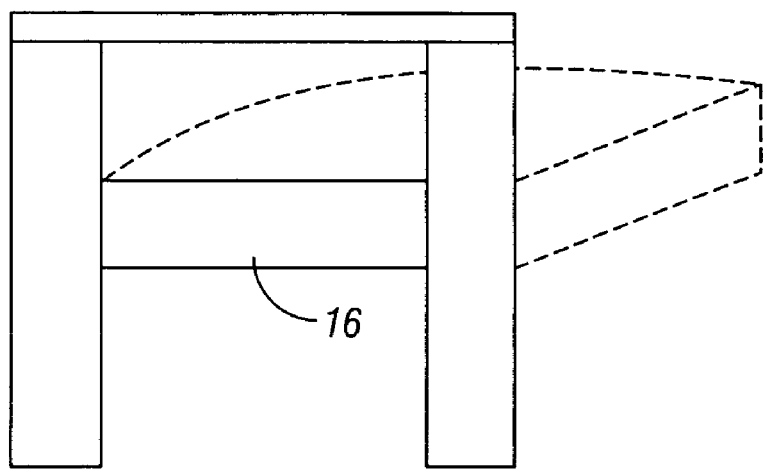
FIG. 2 is a schematic of a second portal arrangement disclosed in the parent patent applications.
Figure 3:
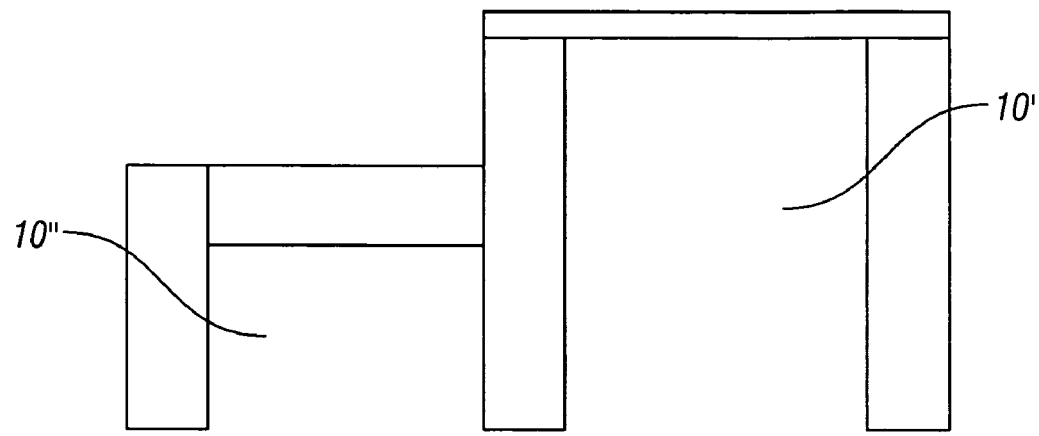
FIG. 3 is a schematic of a third portal arrangement disclosed in the parent patent applications.

Alternatively, in addition to the vertically arranged sensor panels as in the aforementioned known portals, the portal can have a "dutch door" with an additional, horizontal, sensor panel 16 in the upper half of the door, just high enough to clear a patient on a gurney, as shown in FIG. 2. As the patient is wheeled under the upper door, the patient would pass in close proximity to the horizontal sensor panel 16, allowing all of its sensors to scan the patient from head to foot, or vice versa. This gives the best detection and resolution of objects, since more sensors are placed closer to the patient. Then, the attendant would push the dutch door open and walk through the portal, being scanned by the vertically arranged sensor panels. The "dutch door" array 16 can be spring loaded, so that it moves out of the way for an ambulatory subject. A microswitch indicator can tell the software whether the door is engaged, for a recumbent patient, or disengaged, for an ambulatory subject. As a variation of this, a portal with vertically arranged sensor panels can be situated next to a portal with a horizontally arranged sensor panel, as shown in FIG. 3.

As an alternative to the passive magnetic portal, an AC or DC magnetizing field can be provided by one or more source coils, a DC field can be provided by a permanent magnet array, or a DC field can be provided in the form of the fringing field of a nearby MRI magnet. In any case, a computer is provided to interrogate the sensors and to interpret the magnetic signals, to detect, characterize, and locate ferromagnetic objects. Characterization of the object provides the size and orientation of its magnetic moment, which can be related to the physical size of the object, and to the magnitude of the attractive magnetic force. The analysis software can use various known algorithms, or a neural network can be used. The information gained can be related to a photographic image of the subject, for the purpose of locating the ferromagnetic object on the subject. A light display can be used to indicate the approximate location of the detected object. System diagnosis, monitoring, and signal interpretation can be done via the Internet, if desired.

As an alternative to the portal type screening apparatus, a hand-held device can be used to screen individuals specifically for strongly paramagnetic or ferromagnetic objects they may be carrying or wearing, before they enter the high-field region of an MRI suite. In some instances, the lack of floor space precludes a fixed installation such as the portal disclosed above. In these cases, a hand wand may be preferred.

The hand-held device, or wand, comprises a compact magnetic gradiometer and its electronics. The gradiometer can measure either a single gradient component, multiple components, or the complete gradient tensor. The gradiometer comprises one or more pairs of magnetic sensors and reads out the difference signal between members of each pair. Background fields have small gradients, so the difference signal resulting from these is small. Close to a paramagnetic or ferromagnetic body, however, field gradients are strong; they vary as $1/r^4$ with the distance r from the sensor to the magnetic body. A strong anomaly is sensed whenever the wand is passed close by such an object of interest. The wand does not detect nonmagnetic metals. Its electronics read the signals out and process them. The output can be in the form of a simple alarm when the signal exceeds a threshold. More robust processing algorithms can incorporate adaptive background cancellation to further suppress background gradient interference, and target-object localization in the case of full tensor gradiometer implementations.

To increase the signal from the target object, it can be desirable to make the measurement in a stronger ambient field than the earth's magnetic field, which is about 0.5 Gauss. The fringing field from a magnetic resonance imaging (MRI) magnet can provide such an enhanced field, with strengths in excess of 10 Gauss.

A further example combines the magnetic wand with a wire coil that can be used, by means of driving electric current through it, to generate a controlled source field. The coil can be configured to suppress its common-mode signal on the gradiometer sensors but provide a magnetizing field around the wand. This field, by magnetizing paramagnetic or ferromagnetic objects, increases their signal relative to the background. The field can be static (DC) or time-varying (AC). The benefit of an AC field is that the system can work at a non-zero frequency, further suppressing background interference. The frequency is chosen to be low enough, however, not to excite a response from conductive but nonmagnetic objects.

This device consists of a rigid, non-metallic, non-magnetic structure that supports one or more pairs of magnetometers. Each pair consists of sensors aligned to measure the same component of the magnetic field. Each pair's two outputs are differenced to create the gradient signal. Sensor electronics operate the sensors and perform the differencing. They also operate signal processing algorithms to suppress background interference and to alarm in the proximity of paramagnetic or ferromagnetic objects.

In use of an active magnetic source, the wand also has one or more coils of wire and electronics to drive controlled currents in the coils, to act as a magnetizing source field. The coils are designed to produce a substantially zero differential signal on the gradiometers, in the absence of nearby magnetic objects.

In a further example, an applied DC magnetic field can be created by means of one or more permanent magnets mounted in the wand. Both AC and DC instruments measure magnetic fields, but in different ways. The magnets are mounted such that their primary magnetic field is oriented substantially orthogonally to the sensitive axis of the magnetometers in the wand. In this way, the sensors are not saturated by the applied DC field, but remain sensitive to enhanced magnetization of a ferromagnetic object by that field. Use of permanent magnets to generate the field has an advantage over using a coil, namely, the permanent magnet draws no power. However, a potential disadvantage is that the magnetic field cannot be turned off, so the wand must be stored carefully when not in use.

The use of AC fields enables the use of induction coil sensors, in addition to or instead of magnetometers, like magnetoresistive, fluxgate, and other types. Induction coil sensors are impossible to use in the DC field because the induction coil has zero sensitivity at zero frequency. Using induction coil sensors typically reduces the cost of the product without sacrificing sensitivity in the AC system. Using induction coil sensors confers a particular advantage, in that it renders the wand insensitive to interference from noise induced by the wand's motion in the Earth's field. This is a major potential source of interference in the case of the DC applied field.

An AC system could make use of two different excitation directions—operating at two different frequencies, to avoid crosstalk—which can improve detection of long, narrow objects, which are precisely the shape that is most dangerous in this situation.

The wand can be extended into a two-dimensional array of sensors to enable reliable scanning without as much moving of the wand back and forth. Too large an array becomes unwieldy and expensive; the optimum array size depends upon the balance between cost, reliability, and user skill found in any given application.

Figure 4:
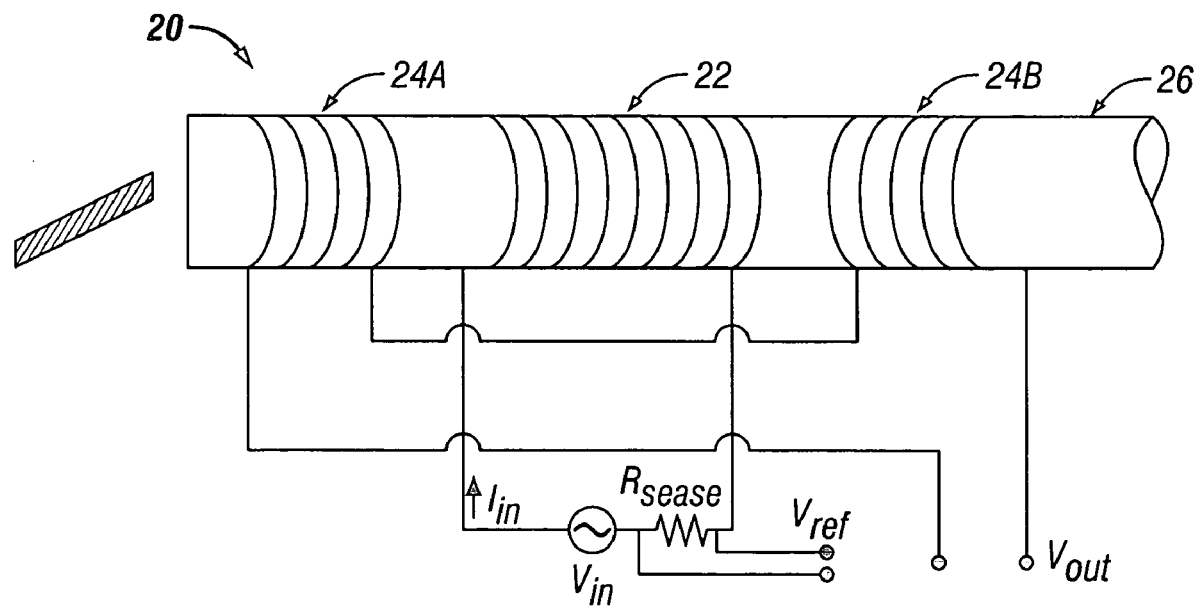
FIG. 4 is a schematic of a first wand arrangement disclosed in the parent patent applications.
Figure 5:
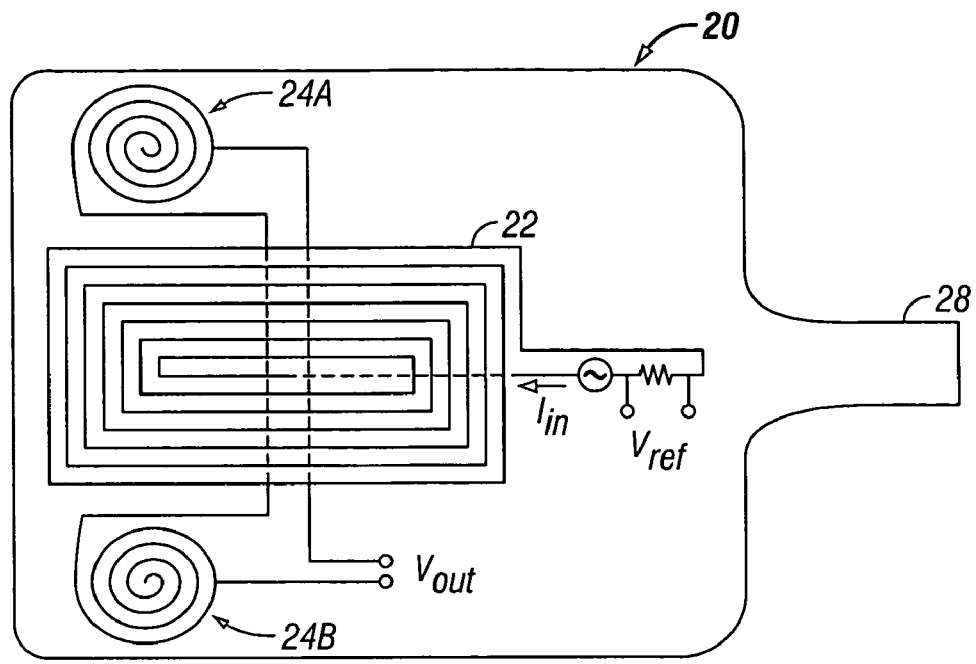
FIG. 5 is a schematic of a second wand arrangement disclosed in the parent patent applications.

FIGS. 4 and 5 illustrate the principles of the wand 20, utilizing an AC source. An excitation coil 22, by means of a sinusoidal (AC) current driven in it, generates an alternating magnetic field that excites a combination of magnetization current and electrical eddy current in any conductive and/or ferromagnetic and/or magnetically permeable body nearby. The excitation frequency is chosen to be low enough so that the magnetization (or, equivalently, magnetic susceptibility) response of objects to be detected exceeds their eddy current response. The choice of frequency is expected to be several tens of hertz (Hz), or at least substantially less than 1 kHz.

The excitation current can be driven by any number of standard drive circuits, including either direct drive (controlled voltage source in series with the coil) or a resonant drive (voltage source coupled to the coil via a series capacitance whose value is chosen such that, in combination with the coil's self-inductance, the current is a maximum at a desired resonant frequency given by $\frac{1}{2}\pi(LC)^{1/2}$).

In both FIGS. 4 and 5, the receiver or sensor coil is, in fact, made of two coils 24A and 24B, wound in opposite senses and connected in series. They form what is well-known as a gradiometer; a uniform magnetic flux threading both coils produces zero response. Coils 24A and 24B are distributed symmetrically about the excitation coil 22 such that, in the absence of any target object (which is conductive, magnetic or magnetically permeable) nearby, each senses an identical flux from the excitation which thus cancels out. A handle 28 can contain the electronics and a battery.

Although the intent is to make the two coils 24A and 24B perfectly identical, and to place them in identically symmetric locations, in practice one falls short of the ideal. As a result, any actual device will display a nonzero response to the excitation, even in the absence of a target; this residual common-mode signal is referred to as an "imbalance" signal. Standard electrical circuits can zero out the imbalance signal by adding an appropriately scaled fraction of the reference voltage $V_{ref}$ (a voltage proportional to the excitation current, obtained by measuring across a series monitor resistor) to the output voltage $V_{out}$.

When a target object is near to either coil 24A or 24B, it spoils the symmetry and thus induces a finite signal. This signal oscillates at the same frequency as the excitation. Standard demodulation or phase-sensitive detection circuits, using $V_{ref}$ as the phase reference, measure the magnitude of $V_{out}$ in phase with $V_{ref}$ and in quadrature (90 degrees out of phase) with $V_{ref}$. At an appropriately chosen low frequency, the response will be dominated by the susceptibility response, which appears predominantly in the quadrature output, as opposed to the eddy current response, which appears predominantly in the in-phase component.

In principle, the coils 24A and 24B could be replaced by two magnetometer sensors (fluxgate, magnetoresistive, magnetoimpedance, etc.). Coils respond to the time derivative of the magnetic field, while magnetometers respond to the field itself; the coil's output voltage is shifted by 90 degrees with respect to a magnetometer's. If magnetometers are used instead of coils, then the susceptibility response would show up in the in-phase component and the eddy current response (at low frequency) in the quadrature component.

If the operating frequency is chosen much too high, both susceptibility and eddy-current responses appear in the in-phase component (using magnetometers) or quadrature component (using coils), but with opposite sign, making it impossible to distinguish between the two. At intermediate frequencies, the eddy current phase is intermediate between the two components, complicating the distinction. Therefore, it is important to choose the excitation frequency to be low enough, and preferably less than about 1000 Hz.

The substrate or coil form 26 must be nonconductive, nonferromagnetic and, with one possible exception, magnetically impermeable ($\mu=\mu_o$, where $\mu_o$ is the permeability of free space). The exception is that a magnetically permeable core inside the sense coils 24A, 24B (practical only in the cylindrical geometry of FIG. 4) can increase the sensitivity of the system.

Using a resonant drive circuit for the excitation coil 22 may significantly reduce the electrical power needed to create the excitation. Thus, this may be preferred for a battery-operated, hand-held wand. The other circuits, including demodulation, threshold, discrimination, and alarm/alert, require negligible power, so the system power is dominated by the excitation requirement.

Figure 6:
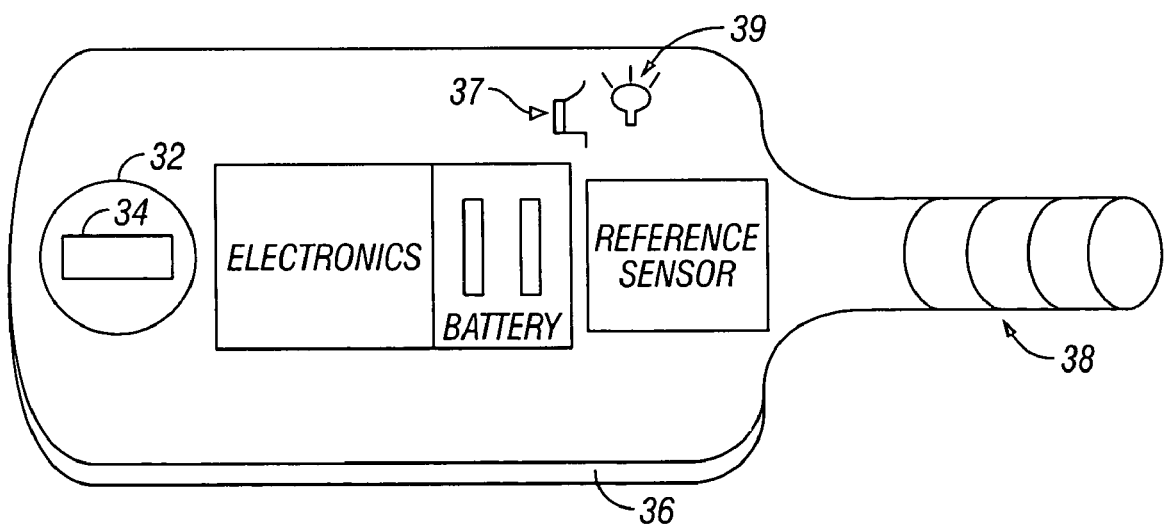
FIG. 6 is a schematic of a third wand arrangement disclosed in the parent patent applications.

As shown in FIG. 6, the DC wand 30 can have a sensor board with 2 sensors 34, which can be placed at each end of an epoxy fiberglass paddle 36. A DC magnetic field source 32, such as a permanent magnet, an example of which is a ferrite disc, can be mounted in such a manner as to provide a substantially normal (perpendicular) magnetic field at the sensor 34. The concept of this arrangement is to provide an external magnetic field source to induce magnetization in any local ferromagnetic body, so that the sensor 34 can detect that body, while, at the same time providing no in-the-plane-of-the-sensor active-axis magnetic field.

The use of a reference sensor helps to eliminate common mode error signals. For instance, a nearby passenger conveyer, such as a gurney, could contain magnetic components, but this spurious magnetization is not what is intended to detect, and, therefore, it is preferable to eliminate this magnetic source.

An audio alert 37, such as a buzzer, and/or an alarm light 39 can be employed to signal the presence of an unwanted ferromagnetic object. A ferromagnetic bobby pin is an example of such an unwanted ferromagnetic object.

A non-ferromagnetic covering material, constructed, for instance, of a substance such as aluminum or nylon, or other suitable material, can surround the wand 30. This type of covering is not only protective; it also facilitates removal of any ferromagnetic objects which might stick to the wand.

Figure 7:
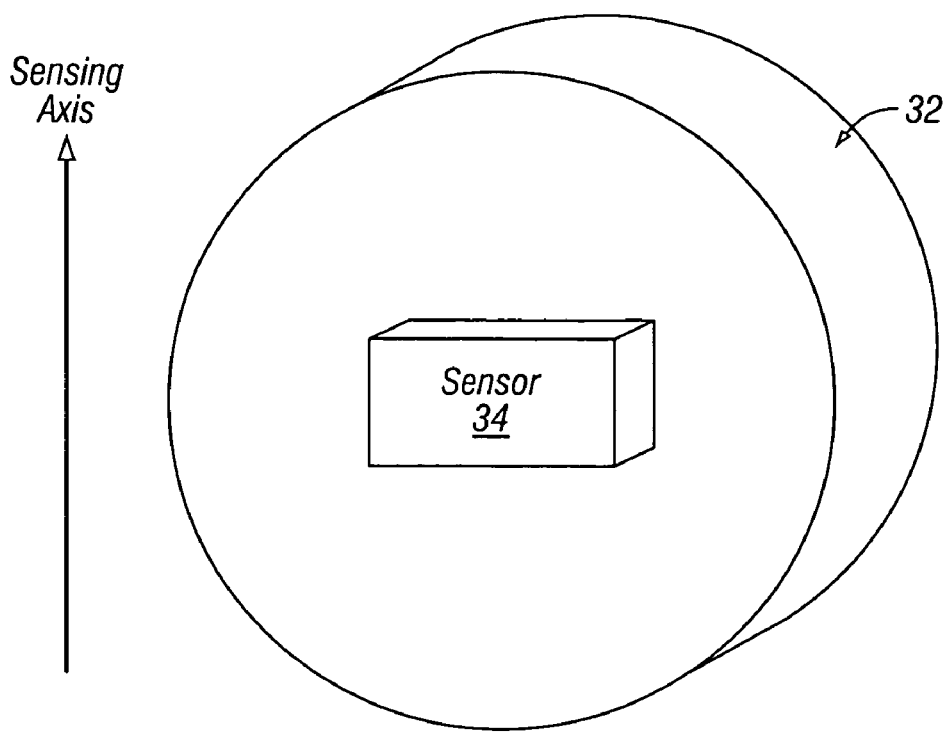
FIGS. 7 through 10 are schematics of several arrangements of the source fields and sensors disclosed in the parent patent applications.

As shown in FIG. 7, the sensor's sensitivity axis is substantially orthogonal to the axis of the magnetic field of the permanent magnet 32. Otherwise stated, the magnetic field of the permanent magnet 32 is normal to the plane of the sensor 34.

Figure 8:
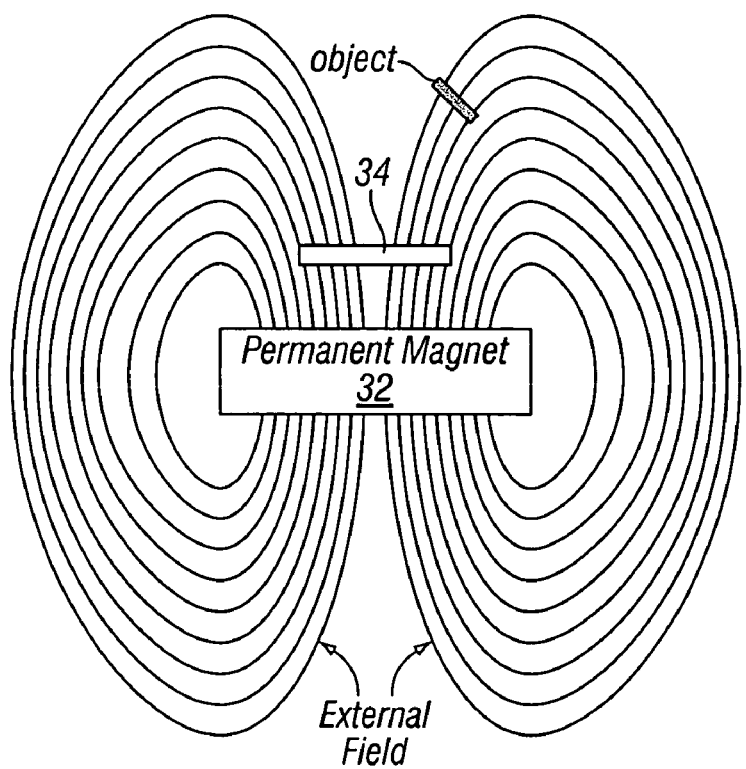
Figure 9:
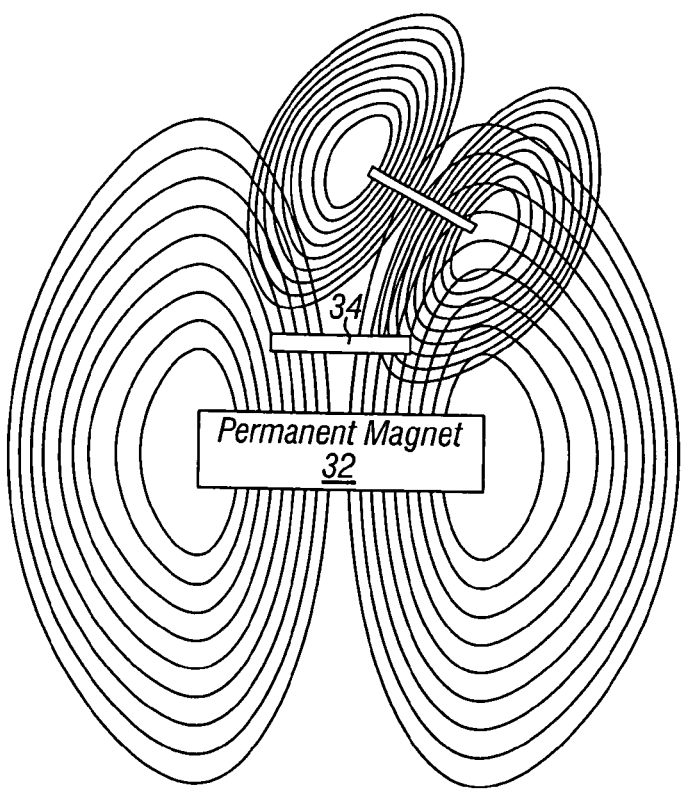

In FIG. 8, the magnetic field of the DC permanent magnet field source 32 magnetizes the ferromagnetic object, which then has a magnetic field of its own, as shown in FIG. 9. This induced magnetization ("demag field") is detected by the sensor 34, triggering the alarm buzzer 37 and/or light 39.

Figure 10:
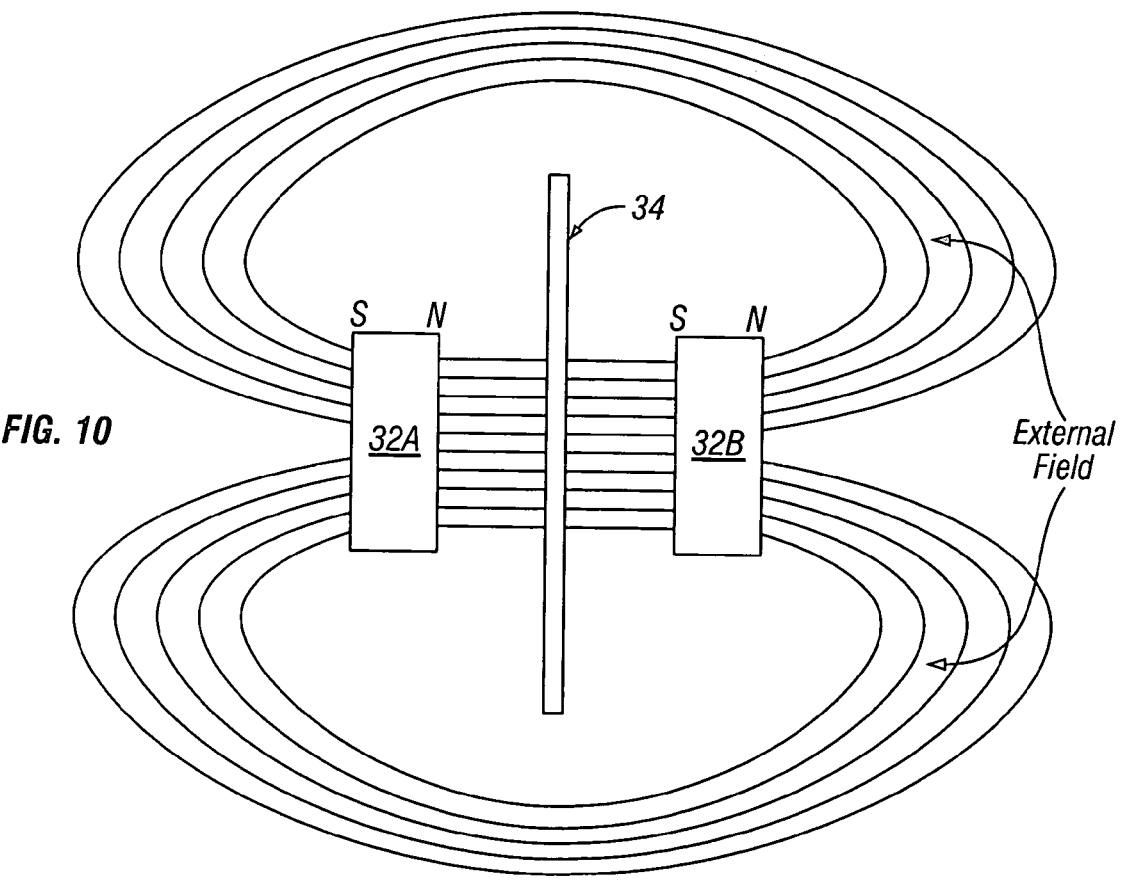

An alternative wand configuration, shown in FIG. 10, utilizes two permanent magnets 32A, 32B, as the magnetic field between them is less divergent than with a single permanent magnet. With the use of two permanent magnets 32A, 32B and less resultant divergence, there is less need for criticality about positioning the permanent magnet with respect to the sensor 34.

According to the present invention, it is preferred that a magnetic field strength of 100 Gauss be present at the location of the ferromagnetic threat to be detected, although somewhat larger magnetic field strengths can be non-preferentially employed, such as 200 to 300 Gauss, or somewhat smaller, such as 5 to 40 Gauss. However, it should be kept in mind that large magnetic field strengths can move a relatively non-secured ferromagnetic threat object, such as a retained ferromagnetic foreign particle within the eye, or a ferromagnetic aneurysm clip, or a surgical instrument. In addition, a large magnetic field strength can adversely affect pacemakers and other bio-stimulation devices. Conversely, a smaller magnetic field strength may not supply sufficient induced magnetization to allow reliable detection.

Figure 11:
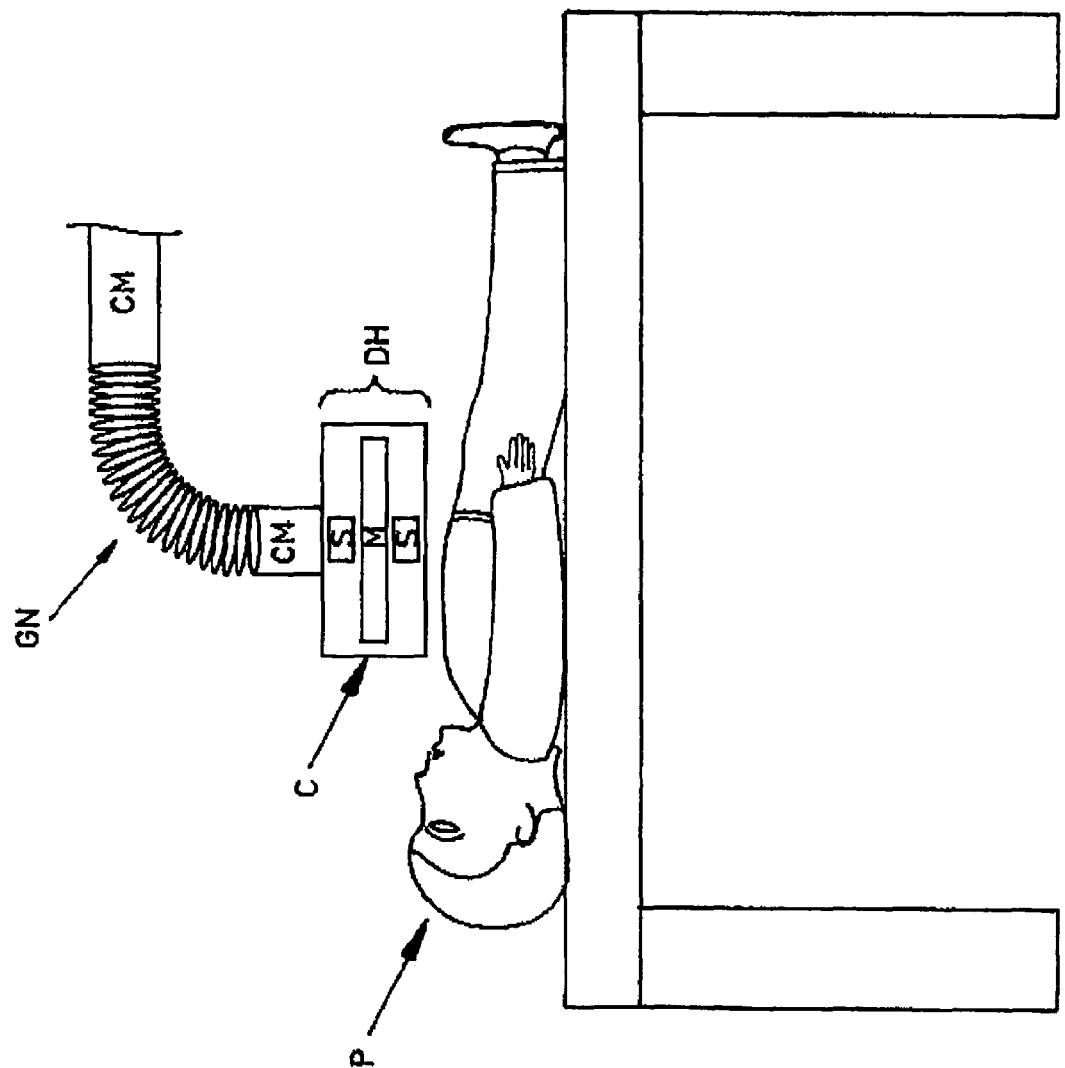
FIG. 11 is a sketch of a first embodiment of the newly disclosed arm-supported apparatus according to the present invention.
Figure 12:
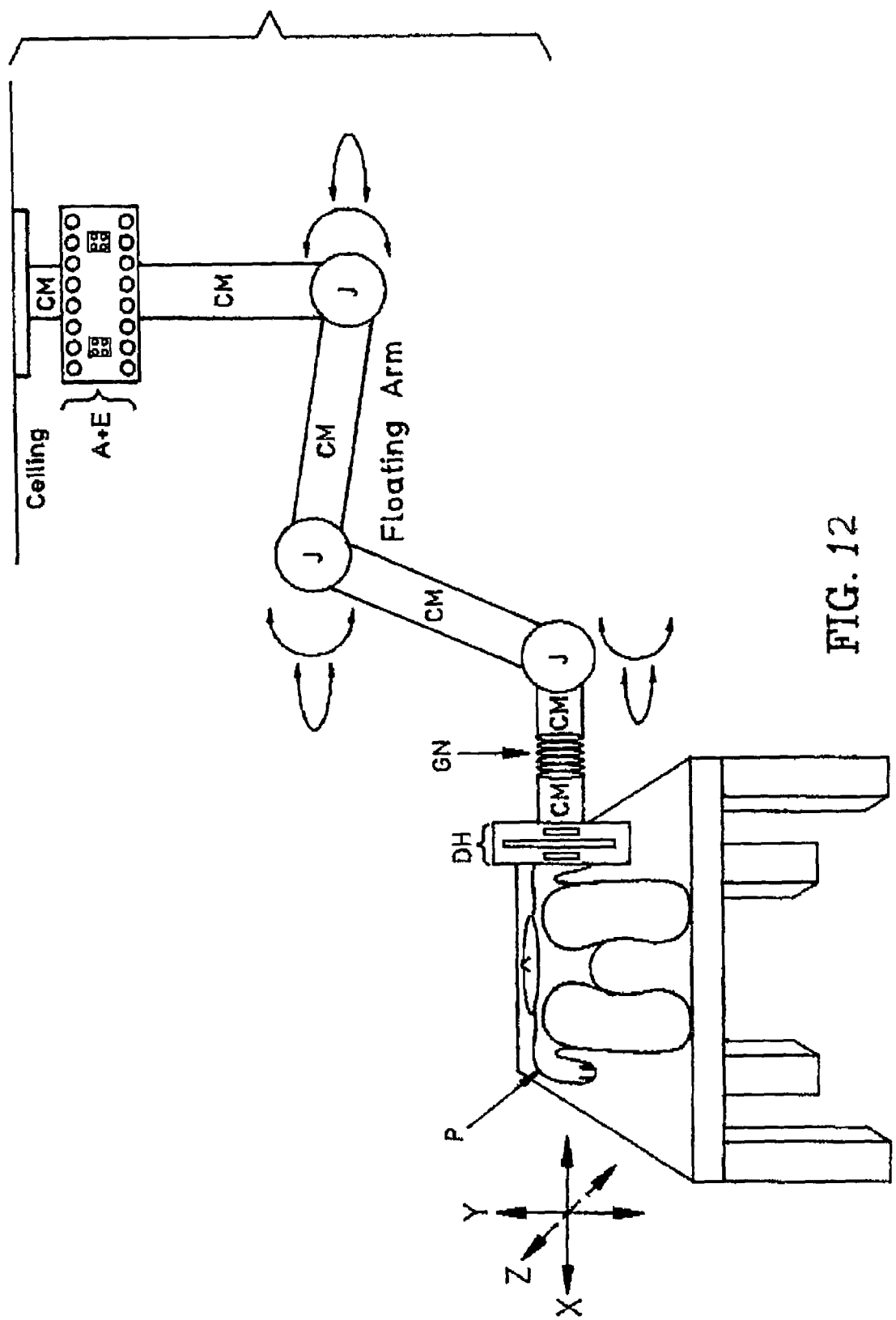
FIG. 12 is a sketch of a second embodiment of the newly disclosed arm-supported apparatus according to the present invention.

As shown in Fig. 11, the sensor pair S, the applied magnetic field source M, and part, or all, of the required electronics can be mounted in a detection head DH. Preferably, the detection head configuration DH is housed in a non-ferromagnetic casing C, such as of aluminum or of plastic. This casing C shields the sensor pair S from the outside environment and prevents air currents from intruding, as air currents create temperature differences which adversely affect sensor performance, decreasing sensitivity. The detection head DH is mounted to a frame connecting member CM of an adjustable arm type support structure, which can incorporate a goose-neck type flexible joint GN. Alternatively, or in conjunction with the goose-neck joint GN, as shown in FIG. 12, one or more ball-joints J can be employed, or any other type of articulating joint.

Positioning the detection head DH as close as possible to any possible location of a ferromagnetic threat object is very important, as this greatly increases detectability, since the sensed signal from a ferromagnetic threat object decreases proportionally with the cube of the distance between the sensors and the threat object (twice the distance yields one-eighth the signal).

For intra-operative MRI applications, the magnetization source M, the sensor configuration S, and the associated electronics comprising the detection head configuration DH of the present invention generally operate in a sterile surgical field. Therefore, the detection head configuration DH must be amenable to being wrapped in a sterile drape, or "baggie." The detection head configuration DH can then be moved into very close proximity, and even touch, the patient P without risk of contamination.

For an obese patient, a ferromagnetic instrument may be lodged deep within a body cavity, such as the abdomen. In this instance, detection must occur at a distance up to 16 or 18 inches, or at an even greater distance for a truly morbidly obese patient. In neurosurgery, however, the maximum distance required for detection is the diameter of the skull, typically approximately 8 inches. As an intra-operative MRI neurosurgical suite is, in many facilities, used only for this single purpose, the present invention can be configured for this neurosurgical application with a magnetization source of different, and generally smaller, dimensions than that required for intra-operative MRI with abdominal surgery.

Depending, then, upon the required depth at which induced magnetization must be effective, the size and the strength of the magnetization source can vary. It is evident that detection of a ferromagnetic threat at a depth of 18 inches within the intra-abdominal cavity is a significantly greater challenge than detection of that same threat object at a depth of 4 inches within the brain. For detecting ferromagnetic threats, such as a retained ferromagnetic instrument or shrapnel deeply embedded within the abdomen, it is generally required that the magnetization source M, and therefore the detection head DH, be larger and, therefore, more unwieldy. For instance, with a DC susceptometer embodiment employing a permanent magnet, the required magnet increases in size, and generally both in diameter and in thickness, as the intended depth of detection increases, making the detection head configuration DH significantly larger for intra-abdominal ferromagnetic detection than that required for ferromagnetic detection within the skull or brain region. The strength of the magnetic field generally scales with the volume of the magnet employed, so an area of detection interest at a greater distance requires a larger magnet than that required for a closer area of detection interest.

If a permanent magnet is used for the magnetization source M, an important reason for increasing its diameter is that the magnetic field strength at the surface of the magnet can be reduced compared to a smaller diameter magnet. For instance, if a magnet with a 4 inch diameter is utilized to provide a magnetic field strength at one foot of 100 Gauss, the magnetic field strength at the surface of this magnet is very large, such as even up to between 1,000 and 3,000 Gauss, and sometimes higher still. This strength poses a danger related to the potential for causing movement of a ferromagnetic threat object. If, on the other hand, the diameter of the magnet is enlarged, such as to 8 to 14 inches, while still providing 100 Gauss at one foot, the magnetic field strength at the surface is typically only 100 to 400 Gauss, a much safer situation.

To accomplish the appropriate movements, as shown in FIG. 12, the detection head configuration DH is mounted onto an adjustable arm support structure, which is preferentially non-ferromagnetic, in such a manner that the detection head configuration DH can be suspended over the patient P, as shown in FIG. 11, or placed along the side of the desired body region of the patient P, as shown in FIG. 12. When required, the detection head configuration DH can be positioned under the patient P, provided that the stretcher upon which the patient is recumbent accommodates this.

The detection head configuration DH can be affixed to an adjustable arm having one or more articulating joints J, or one or more flexible goose-neck structures GN, or a combination thereof, in such a way that the detection head configuration DH can be tilted and moved to and fro in all directions, as well as rotationally, for proper positioning. Orientation and movement along three non-parallel and non-coplanar axes is preferred, as illustrated by the axes X, Y, Z in FIG. 12. In other words, none of the three axes is parallel to either of the other two. Further, in this context, the meaning of "non-coplanar" is that at least one of the three axes is not co-planar with the other two. The axes may or may not intersect. It is preferred that the goose-neck structure GN and the articulating joints J be non-ferromagnetic.

The articulating elements, whether goose-neck elements GN, or other articulating joints J, allow this multi-axis flexure of the detection head configuration DH. The articulating elements are attached to a support structure via appropriate connecting members CM. As shown in FIG. 12, the structure can be attached to the ceiling or other architectural element. Alternatively, it can be attached to any sufficiently heavy object to provide the necessary support. The electronics E and the alarm A can be carried by the same structure or separately mounted. The alarm A can have both audio and visual alarms.

For intra-operative MRI, the support structure is preferably mounted to a non-moveable structure to maintain a safe distance between the detection head configuration DH and the MRI magnet, to prevent the instrument itself from becoming a missile threat. For use in conventional MRI in a non-surgical setting, the support structure may also be mounted to the building structure. In addition, if the instrument is in a room safely away from the MRI magnet, the mounting base may be on wheels, to allow the entire assembly to be moved into and out of position for easy use, and for storage. The support structure can, when appropriate, also be attached to a table, or to another instrument, provided that these are strong enough to provide necessary stability.

The following movements are those which are generally recommended for ferromagnetic threat detection of a patient P and, if desired, of the patient's immediate environs, such as the top of a gurney or stretcher. These movements can be performed in like fashion for either intra-operative MRI, or as a pre-screening procedure prior to conventional MRI. Starting from a reference point relative to the top of the patient P, as shown in FIG. 2, ferromagnetic screening proceeds as follows:

1. up and/or down in a vertical direction relative to the patient P;
2. left and/or right transversely across the patient P; and
3. in one or both directions parallel to the head-foot axis of the patient P.

If the sensor system S is comprised of magneto-resistive sensors, the sensed field from the ferromagnetic threat object is substantially in the plane perpendicular to the primary field of the magnet. For instance, assuming three mutually orthogonal axes, when the primary field of the magnetization source is in the y axis, the sensed field is substantially in the x axis and in the z axis. With a single-axis sensor system, the x and y axes will not be sensed at the same time, but will be sensed separately as a function of the appropriate movements of the detection head configuration DH, while both axes can be sensed simultaneously with an appropriate multi-axis sensor system. On the other hand, if the sensors S are of the saturation resistant variety, the sensed field is substantially parallel to the primary field of the magnet, or the y axis.

So, at each selected position, the detection head DH can be oriented so that the axis of the magnetic field is arranged along each of three axes and moved along each of the axes, in either one or both directions. In addition, after the above described movements, the detection head configuration DH can be moved into a new starting position relative to the patient P, and the orientation and movements can be repeated.

It is acceptable to substitute other movements while searching for ferromagnetic threat objects. For instance, with a starting position from the top of the patient P, screening can proceed from left to right obliquely across the patient P, such as from the patient's left shoulder to the patient's right hip, and so on, or even from the underside, if allowed by the gurney in question. The use of body movement, whenever feasible, such as having the patient P actively tilt and/or rotate his or her head, or, alternatively, having the technician perform these movements on the patient, increases the likelihood of ferromagnetic detection and diminishes the possibility of a false negative.

The advantage of rotating the detection head DH and repeating the screening movements with a different axis of magnetization is that a ferromagnetic threat is much less likely to escape detection. Screening from various starting axes is especially helpful when searching intra-abdominally for ferromagnetic threat objects, especially as one starting position may be significantly closer to a ferromagnetic threat object than another starting position.

The sensors comprising the gradiometer pair are arranged symmetrically relative to the magnetization source, and the two sensors are connected in such a way as to cancel out their respective signals resulting from exposure to the magnetic field of the magnetization source.

Although a single-axis sensor system can be utilized, the use of multi-axis sensors, such as 2-axis, or 3-axis, is a preferred embodiment of the present invention. For 3-axis sensing, 3 pairs of sensors can be used, with each pair sensing a different magnetic field component. Each pair of sensors is preferentially configured in gradiometer format to minimize, or eliminate, unwanted signals from distant moving ferromagnetic sources.

Figure 13:
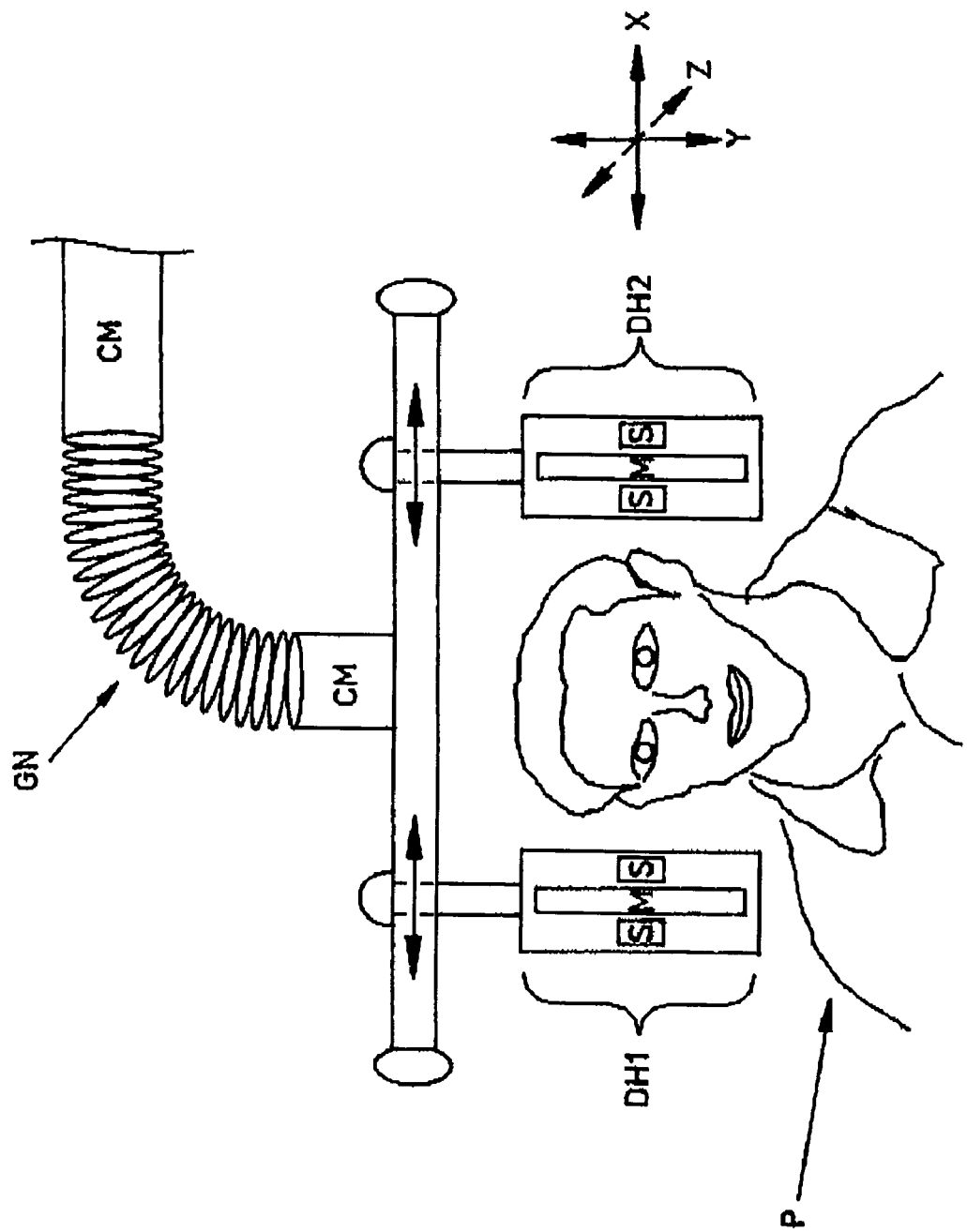
FIG. 13 is a sketch of a third embodiment of the newly disclosed arm-supported apparatus according to the present invention.

An alternative embodiment of the present invention consists of a pair of detection heads DH1 and DH2 working together, as shown in FIG. 13. The two detection heads DH1, DH2 are mounted, spaced apart, to a frame which is in turn mounted to the adjustable arm support structure. Each detection head DH1, DH2 contains an applied field source M and a sensor system S. In this configuration, it is preferred that the detection heads HD1, HD2 are arranged so that the axes of the magnetic fields are arranged substantially parallel to, or even co-linear with, one another to avoid imbalance problems. However, the spacing between the detection heads HD1, HD2 can vary with a slide mechanism. In order to prevent a null in the center area between the two detection head configurations DH1, DH2, the direction of magnetization by the applied field AF is preferred to be in the same direction for both detection heads DH1, DH2. This prevents the cancellation effect of the magnetic field which could occur in the central zone if the directions of magnetization of the magnetizing sources M were to be in opposite directions. The sensor system S of each detection head DH1, DH2 is preferably arranged and connected in gradiometer format.

To use the type of apparatus having two detection heads, the area of interest of the patient P, such as the head, is appropriately centered between the detection heads DH1, DH2. The supporting frame can then be moved, such as in an up-and-down vertical direction, and in a horizontal back-and-forth direction. For these movements, each detection head HD1, HD2 moves in tandem with its mate. If a space is present between each detection head HD1, HD2 and the head of the patient P, in-and-out movements relative to the head of the patient P are also possible. In addition, and very importantly, when a space is created, this allows head tilting and/or rotation, which can increase detectability. The frame can then be rotated either clockwise or counterclockwise, and the movements can be repeated. For instance, the sides of the head of the patient P can be screened, and, after rotation of the "headphone" configuration HP, the front and back of the head of the patient P can also be screened.

The detection head configuration DH of the present invention can be positioned very close to the patient P, and, generally, much closer than can a portal. For instance, a portal with a pass-through aperture sufficient to accommodate a patient on a gurney, such as during intra-operative MRI surgery, cannot get nearly as close to the regions of interest of the patient P as can the present invention. Achieving closeness to a ferromagnetic threat increases detection sensitivity, since the induced magnetization signal from a ferromagnetic threat decreases to the cube of the distance; namely, twice as far away yields 8 times less induced magnetization signal strength. In fact, because of the amenability of placing a sterile "baggy" placed over the detection head configuration DH, it is acceptable for the detection head configuration DH to touch the sterile field during surgical procedures.

In addition, the frame of the two detection head embodiment of the present invention can be adjusted to widen, or to narrow, the space between the two detection heads, in order to be as close as possible to the area of detection interest. This results in a significant detectability advantage.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. An apparatus for excluding ferromagnetic objects from a safe zone, comprising:
   at least one applied magnetic field source;
   at least one pair of sensors arranged and connected as a gradiometer, each said sensor of said at least one pair being adapted to sense a magnetic field of an object, said magnetic field of said object being an induced magnetic field caused by magnetization of said object by said at least one applied magnetic field source;
   a processor adapted to interpret signals from said at least one pair of sensors; and
   a structure on which said at least one pair of sensors and said at least one applied magnetic field source are mounted, said structure being adapted to selectively position said at least one pair of sensors and said at least one applied magnetic field source in proximity to one or more selected areas of interest, while selectively orienting said at least one pair of sensors and said at least one applied magnetic field source so that the axis of the magnetic field is arranged along a selected axis adjacent each said area of interest, and while selectively moving said at least one pair of sensors and said at least one applied magnetic field source along said selected axis adjacent each said area of interest.

2. The apparatus recited in claim 1, said structure being further adapted to:
   selectively orient said at least one pair of sensors and said applied magnetic field source so that the axis of the magnetic field is arranged along each of three different non-parallel axes adjacent each said area of interest, at least two of said axes being non-coplanar; and
   selectively move said at least one pair of sensors and said at least one applied magnetic field source along each of said three axes.

3. The apparatus recited in claim 1, wherein said mounting structure comprises an adjustable arm, said at least one pair of sensors and said at least one applied magnetic field source being mountable to a first end of said adjustable arm.

4. The apparatus recited in claim 3, wherein a second end of said adjustable arm is fixedly mounted to prevent movement of said arm in response to any magnetic source external to said apparatus.

5. The apparatus recited in claim 3, wherein said adjustable arm comprises a plurality of pivotable joints.

6. The apparatus recited in claim 3, wherein said adjustable arm comprises at least one flexible section.

7. The apparatus recited in claim 1, wherein:
   said mounting structure comprises a frame;
   a first said pair of sensors and a first said magnetic field source are mounted to said frame;
   a second said pair of sensors and a second said magnetic field source are mounted to said frame spaced apart from said first pair of sensors and said first magnetic field source;
   said first magnetic field source and said second magnetic field source are arranged to generate their respective magnetic fields in the same direction, thereby avoiding a region of reduced magnetic field strength therebetween; and
   said frame is adapted to place said first pair of sensors and said first magnetic field source on a first side of a selected said area of interest while placing said second pair of sensors and said second magnetic field source on a second side of said selected area of interest.

8. The apparatus recited in claim 7, wherein said space from said first pair of sensors and said first magnetic field source to said second pair of sensors and said second magnetic field source is adjustable.

9. The apparatus recited in claim 1, further comprising means for connecting said apparatus to the Internet.

10. The apparatus recited in claim 9, further comprising means for monitoring at least one element of a group including said field source, said sensors, said processor and said structure, via the Internet.

11. The apparatus recited in claim 10, further comprising means for diagnosing a condition of said at least one monitored element via the Internet.

12. The apparatus recited in claim 9, further comprising means for interpreting said signals from said at least one pair of sensors, via the Internet.

13. A method for excluding objects from a safe zone, said method comprising:
   providing a processor, at least one applied magnetic field source, and at least one pair of sensors arranged and connected as a gradiometer, said processor, said at least one applied field source and said at least one pair of sensors all being mounted on a structure;
   generating an applied magnetic field with said at least one applied magnetic field source;
   positioning said at least one pair of sensors and said at least one applied magnetic field source in proximity to at least one selected area of interest, while selectively orienting said at least one pair of sensors and said at least one applied magnetic field source so that the axis of the magnetic field is arranged along a selected axis adjacent each said area of interest, and while selectively moving said at least one pair of sensors and said at least one applied magnetic field source along said selected axis adjacent each said area of interest;
   inducing a magnetic field in an object in said selected area of interest with said at least one applied magnetic field;
   sensing said induced magnetic field of said object with said at least one pair of sensors; and
   processing signals from said at least one pair of sensors to detect said object.

14. The method recited in claim 13, further comprising:
   selectively orienting said at least one pair of sensors and said at least one applied magnetic field source so that the axis of the magnetic field is arranged along each of three different non-parallel axes adjacent each said area of interest, at least two of said axes being non-coplanar; and
   selectively moving said at least one pair of sensors and said at least one applied magnetic field source along each of said three axes.

15. The method recited in claim 13, wherein:
   said mounting structure comprises an adjustable arm, said at least one pair of sensors and said at least one applied magnetic field source being mountable to a first end of said adjustable arm; and
   said positioning and movement of said at least one pair of sensors and said at least one magnetic field source are created by manipulating said first end of said adjustable arm in proximity to each said area of interest.

16. The method recited in claim 13, further comprising:
   providing a frame on said mounting structure, with a first said pair of sensors and a first said magnetic field source mounted to said frame, and with a second said pair of sensors and a second said magnetic field source mounted to said frame spaced apart from said first pair of sensors and said first magnetic field source, said magnetic fields generated by said magnetic field sources being aligned in the same direction;

placing said first pair of sensors and said first magnetic field source on a first side of a selected said area of interest;

placing said second pair of sensors and said second magnetic field source on a second side of said selected area of interest;

simultaneously orienting said first and second pairs of sensors and said first and second applied magnetic field sources so that the axes of the magnetic fields are arranged along a selected axis adjacent each said area of interest; and simultaneously moving said first and second pairs of sensors and said first and second applied magnetic field sources along said selected axis adjacent each said area of interest.

17. The method recited in claim 16, further comprising:
simultaneously orienting said first and second pairs of sensors and said first and second applied magnetic field sources so that the axes of the magnetic fields are arranged along each of three different non-parallel axes adjacent each said area of interest, at least two of said axes being non-coplanar; and simultaneously moving said first and second pairs of sensors and said first and second applied magnetic field sources along each of said three axes.

18. The method recited in claim 16, further comprising adjusting the space from said first pair of sensors and said first magnetic field source to said second pair of sensors and said second magnetic field source.

19. The method recited in claim 13, further comprising monitoring at least one element of a group including said field source, said sensors, said processor and said structure, via the Internet.

20. The method recited in claim 19, further comprising diagnosing a condition of said at least one monitored element, via the Internet.

21. The apparatus recited in claim 13, further comprising interpreting said signals from said at least one pair of sensors, via the Internet.

* * * * *